United States Patent
Ellingson et al.

(10) Patent No.: US 10,010,716 B2
(45) Date of Patent: Jul. 3, 2018

(54) IMPLANTABLE MEDICAL DEVICE WITH AUTOMATIC SENSING THRESHOLD ADJUSTMENT IN NOISY ENVIRONMENT

(75) Inventors: Michael L. Ellingson, St. Louis Park, MN (US); Patrick L. Parish, Circle Pines, MN (US); Hyun J. Yoon, Vadnais Heights, MN (US)

(73) Assignee: Medtronic, Inc., Minneapolis, MN (US)

(*) Notice: Subject to any disclaimer, the term of this patent is extended or adjusted under 35 U.S.C. 154(b) by 1027 days.

(21) Appl. No.: 13/096,328

(22) Filed: Apr. 28, 2011

(65) Prior Publication Data
US 2012/0277606 A1 Nov. 1, 2012

(51) Int. Cl.
*A61N 1/37* (2006.01)

(52) U.S. Cl.
CPC .......... *A61N 1/3704* (2013.01); *A61N 1/3718* (2013.01)

(58) Field of Classification Search
CPC ............................ A61N 1/3704; A61N 1/3718
USPC .......................... 607/9, 27, 28; 128/901, 902
See application file for complete search history.

(56) References Cited

U.S. PATENT DOCUMENTS

| | | |
|---|---|---|
| 5,513,644 A | 5/1996 | McClure et al. |
| 5,564,430 A * | 10/1996 | Jacobson et al. ............ 600/510 |
| 5,697,958 A | 12/1997 | Paul et al. |
| 6,029,086 A | 2/2000 | Kim et al. |
| 6,112,119 A | 8/2000 | Schuelke et al. |
| 6,556,859 B1 | 4/2003 | Wohlgemuth et al. |
| 6,745,074 B1 | 6/2004 | Obel |
| 6,745,076 B2 | 6/2004 | Wohlgemuth et al. |
| 7,561,915 B1 | 7/2009 | Cooke et al. |
| 7,693,568 B2 | 4/2010 | Zeijlemaker |
| 7,693,574 B2 | 4/2010 | Wessels |
| 2003/0083570 A1 | 5/2003 | Cho et al. |
| 2006/0085038 A1 | 4/2006 | Linder et al. |
| 2007/0049995 A1 | 3/2007 | Wessels |

(Continued)

FOREIGN PATENT DOCUMENTS

| | | |
|---|---|---|
| EP | 601775 | 6/1994 |
| EP | 1506037 | 9/2010 |

OTHER PUBLICATIONS

Ellingson et al., U.S. Appl. No. 13/095,076, "Pacing in the Presence of Electromagentic Interference", filed Apr. 27, 2011.
(Continued)

*Primary Examiner* — Christopher A Flory

(57) ABSTRACT

An implantable medical system includes an implantable medical lead including at least one electrode and an implantable medical device (IMD) coupled to the implantable medical lead. The IMD includes a sensing module that obtains electrical signals on the implantable medical lead. The electrical signals on the implantable medical lead include cardiac signals as well as noise-induced signals. The IMD also includes a noise detection module that obtains noise signals independently of the electrical signals on the implantable medical lead. A control module of the IMD adjusts a sensing threshold of the sensing module in response to detecting the noise signals via the noise detection module. In instances in which the amplitude of the noise-induced signal on the lead is too large, the IMD may transition to a noise operating mode specifically designed to accommodate noisy environments.

24 Claims, 8 Drawing Sheets

(56) References Cited

U.S. PATENT DOCUMENTS

2007/0238975 A1   10/2007  Zeijlemaker
2011/0077706 A1    3/2011  Ellingson et al.

OTHER PUBLICATIONS

Naehle, et al., "Magnetic Resonance Imaging at 1.5-T in Patients with Implantable Cardioverter-Defibrillators", Journal of the American College of Cardiology, vol. 54, No. 6, 2009, pp. 549-555.
(PCT/US2012/020411) PCT Notification of Transmittal of the International Search Report and the Written Opinion of the International Searching Authority, 10 pages.

* cited by examiner

IMPLANTABLE MEDICAL DEVICE WITH AUTOMATIC SENSING THRESHOLD ADJUSTMENT IN NOISY ENVIRONMENT

TECHNICAL FIELD

The disclosure relates generally to implantable medical devices. In particular, the disclosure describes techniques for improving sensing by an implantable medical device in a noisy environment.

BACKGROUND

A wide variety of implantable medical systems that deliver a therapy or monitor a physiologic condition of a patient have been clinically implanted or proposed for clinical implantation in patients. An example implantable medical system may include an implantable medical lead connected to an implantable medical device (IMD). For example, implantable leads are commonly connected to implantable pacemakers, defibrillators, cardioverters, or the like, to form an implantable cardiac system that provides electrical stimulation to the heart or sensing of electrical activity of the heart. The electrical stimulation pulses can be delivered to the heart and the sensed electrical signals can be sensed by electrodes disposed on the leads, e.g., typically near distal ends of the leads. Implantable leads are also used in neurological devices, muscular stimulation therapy, gastric system stimulators and other implantable medical devices (IMDs).

Patients that have implantable medical systems may benefit, or even require, various medical imaging procedures to obtain images of internal structures of the patient. One common medical imaging procedure is magnetic resonance imaging (MRI). MRI procedures may generate higher resolution and/or better contrast images (particularly of soft tissues) than other medical imaging techniques. MRI procedures also generate these images without delivering ionizing radiation to the body of the patient, and, as a result, MRI procedures may be repeated without exposing the patient to such radiation.

During an MRI procedure, the patient or a particular part of the patient's body is positioned within an MRI device. The MRI device generates a variety of magnetic and electromagnetic fields to obtain the images of the patient, including a static magnetic field, gradient magnetic fields, and radio frequency (RF) fields. The static magnetic field may be generated by a primary magnet within the MRI device and may be present prior to initiation of the MRI procedure. The gradient magnetic fields may be generated by electromagnets of the MRI device and may be present during the MRI procedure. The RF fields may be generated by transmitting/receiving coils of the MRI device and may also be present during the MRI procedure.

If the patient undergoing the MRI procedure has an implantable medical system, the various fields produced by the MRI device may have an effect on the operation of the medical leads and/or the IMD to which the leads are coupled. For example, the gradient magnetic fields or the RF fields generated during the MRI procedure may induce energy on the implantable leads (e.g., in the form of a current). The current induced on the implantable leads may cause the IMD to sense a cardiac signal when one is not present, a phenomenon referred to as oversensing, or to not sense a cardiac signal when one is present, a phenomena referred to as undersensing. Oversensing and undersensing may result in the IMD delivering therapy when it is not desired or withholding therapy when it is desired.

SUMMARY

In general, this disclosure describes techniques to improve sensing by an IMD during exposure to electromagnetic interference (EMI). The IMD adjusts a sensing threshold used to detect cardiac electrical signals in response to detecting noise. In some instances, the IMD may adjust the sensing threshold immediately upon detecting the first instance of noise. The IMD may increase the sensing threshold to a value that is larger than an amplitude of the noise-induced signal and smaller than an amplitude the cardiac signals. In this manner, the sensing threshold is automatically adjusted to a value capable of distinguishing between intrinsic cardiac signals and noise-induced signals. The improved sensing may allow IMD to continue providing pacing therapy as a function of the sensing.

In instances in which the amplitude of the EMI is too large (e.g., larger than the amplitude of intrinsic cardiac signals), the IMD may transition to a noise operating mode specifically designed to accommodate noisy environments. A noise operating mode specifically designed to accommodate noise in an MRI environment may be referred to as an MRI operating mode or an MRI-safe operating mode. In one example, the IMD may transition to operate in an MRI operating mode that provides pacing therapy without relying on sensing, such as an asynchronous pacing mode.

In one example, this disclosure is directed to an implantable medical system comprising an implantable medical lead including at least one electrode and an implantable medical device coupled to the implantable medical lead. The implantable medical device includes a sensing module that obtains electrical signals on the implantable medical lead, wherein the electrical signals include cardiac signals and noise-induced signals. The implantable medical device also includes a noise detection module that obtains noise signals independently of the noise-induced signals on the implantable medical lead. A control module of the implantable medical device adjusts a sensing threshold of the sensing module in response to detecting the noise signals via the noise detection module.

In another example, this disclosure is directed to a method comprising sensing electrical signals on an implantable medical lead, wherein the electrical signals include cardiac signals and noise-induced signals. The method also includes sensing noise signals independently of the noise-induced signals on the implantable medical lead. The method further includes adjusting a sensing threshold used to sense the electrical signals of the implantable medical lead in response to sensing the noise signals independently of the noise-induced signals on the implantable medical lead.

In a further example, this disclosure is directed to a computer-readable medium comprising instructions that, when executed, cause an implantable medical device to sense electrical signals on an implantable medical lead, wherein the electrical signals include cardiac signals and noise-induced signals, sense noise signals independently of the noise-induced signals on the implantable medical lead, and adjust a sensing threshold used to sense the electrical signals of the implantable medical lead in response to sensing the noise signals independently of the noise-induced signals on the implantable medical lead.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
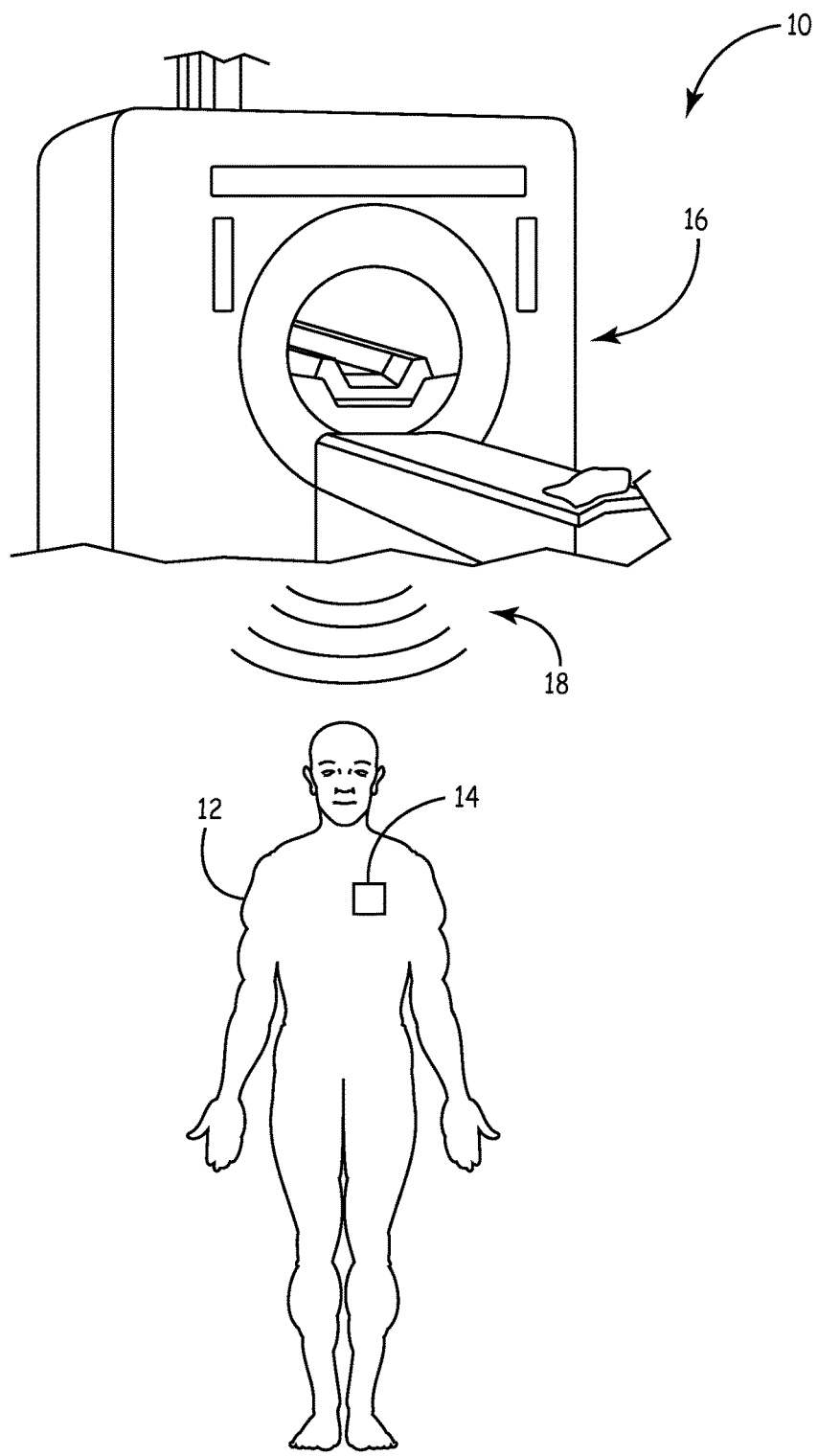
FIG. 1 is a conceptual diagram illustrating an environment in which an implantable medical system is exposed to an external field.

FIG. 1 is a conceptual diagram illustrating an environment 10 in which a patient 12 with an implantable medical system 14 is exposed to an external field 18. In the example illustrated in FIG. 1, environment 10 includes an MRI device 16 that generates external field 18. MRI device 16 generates magnetic and RF fields to produce images of body structures for diagnosing injuries, diseases and/or disorders. In particular, MRI device 16 generates a static magnetic field, gradient magnetic fields and RF fields as is well known in the art. The static magnetic field is a large non time-varying magnetic field that is typically always present around MRI device 16 whether or not an MRI procedure is in progress. Gradient magnetic fields are pulsed magnetic fields that are typically only present while the MRI procedure is in progress. RF fields are pulsed high frequency fields that are also typically only present while the MRI procedure is in progress.

The magnitude, frequency or other characteristic of the static magnetic field, gradient magnetic fields and RF fields may vary based on the type of MRI device producing the field or the type of MRI procedure being performed. A 1.5 T MRI device, for example, will produce a static magnetic field of about 1.5 Tesla (T) and have a corresponding RF frequency of about 64 megahertz (MHz) while a 3.0 T MRI device will produce a static magnetic field of about 3.0 Tesla and have a corresponding RF frequency of about 128 MHz. However, other MRI devices may generate different fields.

Implantable medical system 14 may, in one example, include an IMD connected to one or more leads. The IMD may be an implantable cardiac device that senses electrical activity of a heart of patient 12 and/or provides electrical stimulation therapy to the heart of patient 12. For example, the IMD may be an implantable pacemaker, implantable cardioverter defibrillator (ICD), cardiac resynchronization therapy defibrillator (CRT-D), cardioverter device, or combinations thereof. The IMD may alternatively be a non-cardiac implantable device, such as an implantable neurostimulator or other device that provides electrical stimulation therapy.

During an MRI procedure patient 12 may be placed at least partially within a bore of MRI device 16. Some or all of the various types of fields produced by MRI device 16 (which are represented by external field 18) may create electromagnetic interference (EMI) that has undesirable effects on implantable medical system 14. In one example, the gradient magnetic fields and/or the RF fields generated during the MRI procedure may induce energy on the conductors of the leads (e.g., in the form of a current). The induced energy on the conductors of the leads may sometimes be referred to in this disclosure as noise-induced electrical signals or noise-induced signals. The induced energy on the leads may be conducted to the IMD and inappropriately detected as physiological signals, a phenomenon often referred to as oversensing. The detection of the induced energy on the leads as physiological signals may result in the IMD delivering therapy when it is not desired (e.g., triggering a pacing pulse) or withholding therapy when it is desired (e.g., inhibiting a pacing pulse).

This disclosure describes techniques to improve sensing during exposure to external fields 18 that may induce noise on the lead. The IMD adjusts a sensing threshold used to detect cardiac events in response to detecting noise. In some instances, the IMD may adjust the sensing threshold immediately upon detecting the first instance of noise. The IMD may increase the sensing threshold to a value that is larger than an amplitude of the noise-induced signal(s) on the lead and smaller than the amplitude the cardiac signals. In this manner, the sensing threshold is automatically adjusted to a value capable of distinguishing between the intrinsic cardiac signals and MRI-induced noise. The improved sensing may allow IMD to continue providing pacing therapy as a function of the sensing. In instances in which the amplitude of the EMI is too large (e.g., larger than the amplitude of intrinsic cardiac signals), the IMD may transition to a noise operating mode specifically designed to accommodate noisy environments. A noise operating mode specifically designed to accommodate noise in an MRI environment may be referred to as an MRI operating mode or an MRI-safe operating mode.

Although the techniques of this disclosure are described in the context of environment 10 including an MRI device 16 as the external source, the techniques may be used in other environments with EMI, including but not limited environments during electrocautery procedures, diathermy procedures, ablation procedures, radiation therapy procedures, electrical therapy procedures, or magnetic therapy procedures, or non-medical environments, such as those with RFID readers.

Figure 2:
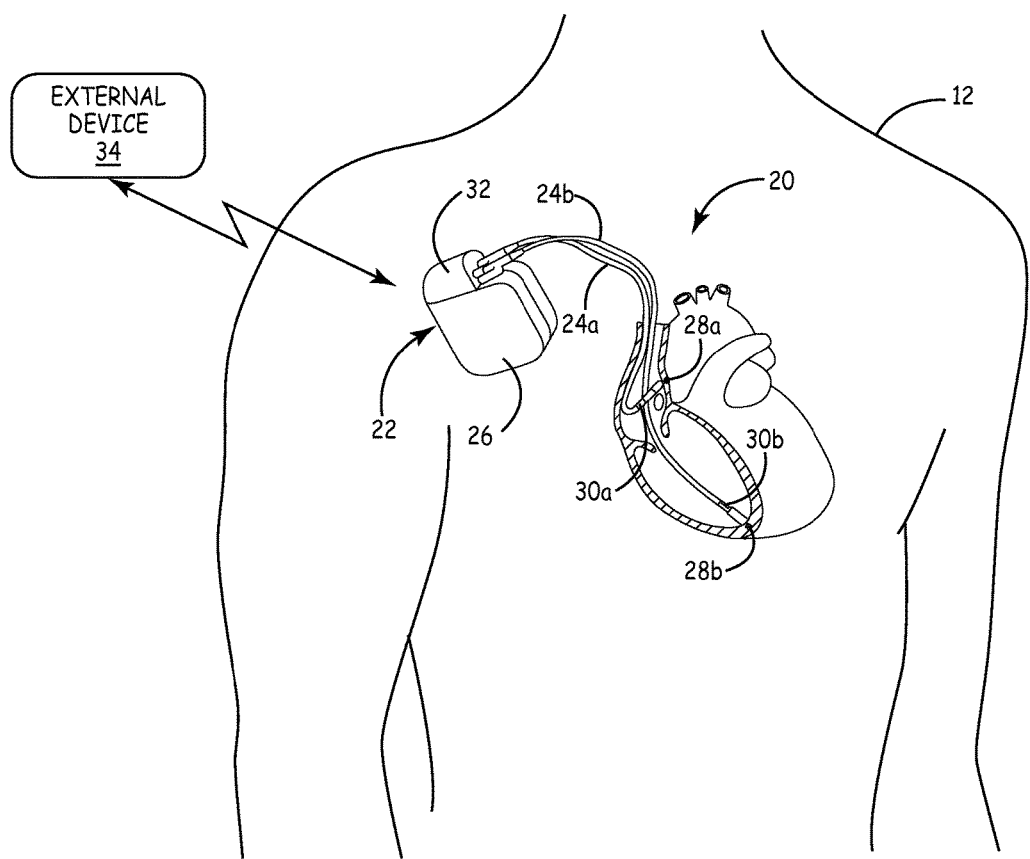
FIG. 2 is a conceptual diagram illustrating an implantable medical system.

FIG. 2 is a conceptual diagram illustrating an example implantable medical system 20. Implantable medical system 20 may correspond with implantable medical system 14 of FIG. 1. Implantable medical system 20 includes an IMD 22 connected to leads 24a,b (sometimes referred to herein as "lead 24"). IMD 22 includes a housing 26 within which electrical components and a power source of IMD 22 are housed. Housing 26 can be formed from conductive materials, non-conductive materials or a combination thereof. As will be described in further detail herein, housing 26 may house one or more processors, memories, transmitters, receivers, transceivers, sensors, sensing circuitry, therapy circuitry, antennas and other components.

Leads 24a,b each includes one or more electrodes. In the example illustrated in FIG. 2, leads 24a,b each include a respective tip electrode 28a,b and ring electrode 30a,b located near a distal end of their respective leads 24a,b. When implanted, tip electrodes 28a,b and/or ring electrodes 30a,b are placed relative to or in a selected tissue, muscle, nerve or other location within the patient 12. In the example illustrated in FIG. 2, tip electrodes 28a,b are extendable helically shaped electrodes to facilitate fixation of the distal end of leads 24a,b to the target location within patient 12. In this manner, tip electrodes 28a,b are formed to define a fixation mechanism. In other embodiments, one or both of tip electrodes 28a,b may be formed to define fixation mechanisms of other structures. In other instances, leads 24a,b may include a fixation mechanism separate from tip electrode 28a,b. Fixation mechanisms can be any appropriate type, including a grapple mechanism, a helical or screw mechanism, a drug-coated connection mechanism in which the drug(s) serves to reduce infection and/or swelling of the tissue, or other attachment mechanism.

Leads 24a,b are connected at a proximal end to IMD 22 via connector block 32. Connector block 32 may include one or more receptacles that interconnect with one or more connector terminals located on the proximal end of leads 24a,b. Leads 24a,b are ultimately electrically connected to one or more of the electrical components within housing 26.

One or more conductors (not shown in FIG. 2) extend within leads 24a,b from connector block 32 along the length of the lead and electrically couple to ring electrodes 30a,b and tip electrodes 28a,b, respectively. In this manner, each of tip electrodes 28a,b and ring electrodes 30a,b is electrically coupled to a respective conductor within its associated lead bodies. For example, a first electrical conductor can extend along the length of the body of lead 24a from connector block 32 and electrically couple to tip electrode 28a and a second electrical conductor can extend along the length of the body of lead 24a from connector block 32 and electrically couple to ring electrode 30a. The respective conductors may electrically couple to circuitry, such as a therapy module or a sensing module, of IMD 22 via connections in connector block 32. IMD 22 delivers therapy to the heart (or other location) via the electrical conductors to one or more of electrodes 28a,b and 30a,b and receives sensed electrical signals on the electrical conductors from one or more of electrodes 28a,b and 30a,b. As will be described in further detail below, the electrical on leads 24 include cardiac electrical signals as well as noise-induced electrical signals.

IMD 22 may communicate with external device 34 to exchange data with external device 34. External device 34 may, for example, communicate with IMD 22 to provide one more operating parameters for operation of IMD 22. IMD 22 may also transmit sensed physiological data, diagnostic determinations made based on the sensed physiological data, IMD performance data and/or IMD integrity data to external device 34. IMD 22 and external device 34 may communicate via wireless communication using any techniques known in the art. Examples of communication techniques may include, for example, inductive telemetry or RF telemetry, although other techniques are also contemplated.

The configuration of implantable medical system 20 illustrated in FIG. 2 is merely an example. In other examples, implantable medical system 20 may include more or fewer leads extending from IMD 22. For example, IMD 22 may be coupled to three leads, e.g., a third lead implanted within a left ventricle of the heart of the patient. In another example, IMD 22 may be coupled to a single lead that is implanted within either an atrium or ventricle of the heart of the patient. As such, IMD 22 may be used for single chamber or multi-chamber cardiac rhythm management therapy.

In addition to more or fewer leads, each of the leads may include more or fewer electrodes. In instances in which IMD 22 is used for therapy other than pacing, e.g., defibrillation or cardioversion, the leads may include elongated electrodes, which may, in some instances, take the form of a coil. IMD 22 may deliver defibrillation or cardioversion shocks to the heart via any combination of the elongated electrodes and housing electrode. As another example, medical system 20 may include leads with a plurality of ring electrodes, e.g., as used in some implantable neurostimulators, without a tip electrode or with one of the ring electrodes functioning as the "tip electrode."

Figure 3:
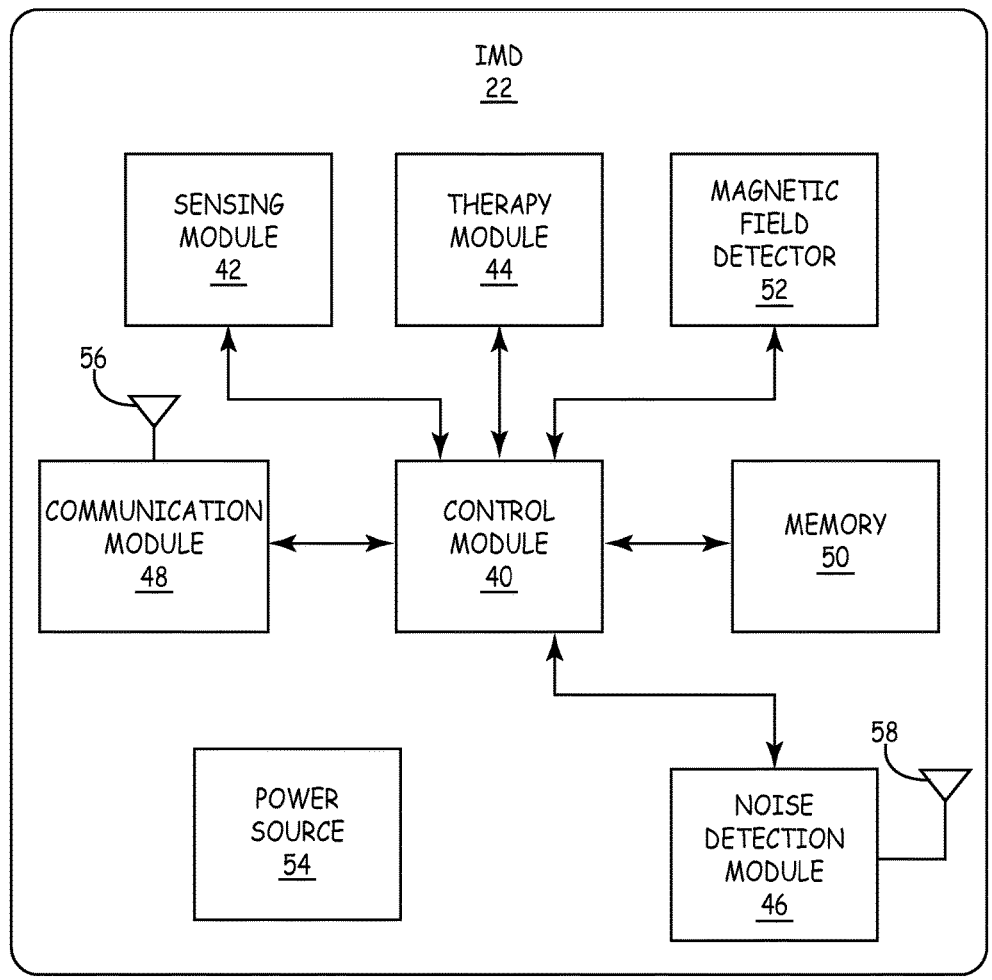
FIG. 3 is a functional block diagram of an example configuration of components of an IMD of an implantable medical system.

FIG. 3 is a functional block diagram of an example configuration of components of IMD 22. In the example illustrated by FIG. 3, IMD 22 includes a control module 40, sensing module 42, therapy module 44, noise detection module 46, communication module 48, memory 50 and magnetic field detector 52. The electronic components may receive power from a power source 54, which may be a rechargeable or non-rechargeable battery. In other embodiments, IMD 22 may include more or fewer electronic components. Additionally, any of the described modules or components may be implemented together on a common hardware component or separately as discrete but interoperable hardware or software components. Depiction of different features as modules or components is intended to highlight different functional aspects and does not necessarily imply that such modules or units must be realized by separate hardware or software components. Rather, functionality associated with one or more modules may be performed by separate hardware or software components, or integrated within common hardware or software components.

Control module 40 may control sensing module 42 and therapy module 44 to operate IMD in accordance with operating parameters of a configured operating mode. Sensing module 42 and therapy module 44 are electrically coupled to some or all of electrodes 28a,b and 30a,b via the conductors of leads 24a,b, or to a housing electrode (e.g., formed from or on housing 26) via conductors internal to housing 26. Control module 40 may select the electrodes that function as sense or therapy electrodes. In one example, control module 40 may configure a switch module to select which of the available electrodes to couple to sensing module 42 and therapy module 44.

Sensing module 42 is configured to obtain signals sensed via one or more of electrodes 28a,b and 30a,b. One or more of electrodes 28a,b and 30a,b (or a housing electrode formed on or integrated as part of housing 26) sense electrical signals attendant to the depolarization and repolarization of the heart. The electrical signals sensed by electrodes 28a,b and 30a,b are conducted to sensing module 42 via one or more conductors of leads 24.

Sensing module 42 includes sensing components used to process signals received from electrodes 28a,b and 30a,b. The components of sensing module 42 may be analog components, digital components or a combination thereof. Sensing module 42 may include multiple sensing channels each having associated sensing components. Each sensing channel may, for example, include one or more sense amplifiers, filters, rectifiers, threshold detectors, analog-to-digital converters (ADCs) or the like. Some sensing channels may convert the sensed signals to digital form and provide the digital signals to control module 40 for processing or analysis. For example, sensing module 42 may amplify signals from the sensing electrodes and convert the amplified signals to multi-bit digital signals by an ADC. Other sensing channels may compare processed signals to a threshold to detect the existence of P- or R-waves and indicate the existence of the P- or R-waves to control module 40.

Control module 40 may process the signals from leads 24a,b to monitor electrical activity of the heart of patient 12. Control module 40 may store signals obtained by sensing module 42 as well as any generated electrogram (EGM) waveforms, marker channel data or other data derived based on the sensed signals in memory 50. Control module 40 may analyze the EGM waveforms and/or marker channel data to detect cardiac events (e.g., tachyarrhythmias). Control module 40 may also later retrieve stored EGMs and/or marker channel data from memory 50 and transmit such information to external device 34.

Under the control of control module 40, communication module 48 may receive downlink telemetry from and send uplink telemetry to external device 34 with the aid of an antenna 56, which may be internal and/or external to IMD 22. Communication module 48 includes any suitable hardware, firmware, software or any combination thereof for communicating with another device, such as external device 34. For example, communication module 48 may include appropriate modulation, demodulation, encoding, decoding, frequency conversion, filtering, and amplifier components for transmission and reception of data.

Therapy module 44 is configured to generate and deliver electrical stimulation therapy to the heart. Control module 40 may control therapy module 44 to deliver electrical stimulation therapy to the heart via one or more of electrodes 28a,b and 30a,b according to one or more therapy programs, which may be stored in memory 50. Control module 40 controls therapy module 44 to deliver electrical pacing pulses, cardiac resynchronization pacing pulses, cardioversion pulses, or defibrillation pulses with the amplitudes, pulse widths, frequencies, electrode combinations or electrode configuration specified by a selected therapy program.

In the case of pacing, therapy module 44 may deliver the pacing therapy as a function of the sensed electrical signals on leads 24. For example, therapy module 44 may utilize the sensed electrical signals (or lack of sensed electrical signals) to trigger delivery of pacing pulses and/or withhold delivery of pacing pulses. In other instances, therapy module 44 may deliver pacing therapy without regard to the sensed electrical signals on leads 24, sometimes referred to as asynchronous pacing.

Therapy module 44 may deliver the pacing pulses via a bipolar electrode configuration, e.g., using tip electrodes 28a,b and ring electrodes 30a,b. In other instances, therapy module 44 may deliver pacing pulses via a unipolar electrode configuration, e.g., using tip electrodes 28a,b and a housing electrode of IMD 22. Therapy module 44 may deliver one or more of these types of stimulation in the form of other signals besides pulses or shocks, such as sine waves, square waves, or other substantially continuous signals.

A patient having implanted medical system 20 may receive a certain therapy or diagnostic technique that exposes implantable medical system 20 to external fields, such as external fields 18 of FIG. 1. In the case of an MRI procedure, for example, implantable medical system 20 is exposed to high frequency RF pulses and various magnetic fields to create image data regarding the patient 12. The RF pulses and/or gradient magnetic fields can induce currents on the conductors of leads 24a,b of the IMD 22, which can be conducted to electrical components of IMD 22, including sensing module 42. In other words, the electrical signals on leads 24a,b include not only cardiac electrical signals, but also noise-induced electrical signals. In some instances, sensing module 42 may incorrectly detect the noise-induced signals as cardiac signals. Inappropriately detecting the EMI- or noise-induced signals on the leads as cardiac signals may have undesirable effects on the pacing therapy provided by therapy module 44, particularly when therapy module 44 delivers the pacing therapy as a function of the sensed electrical signals on leads 24. For example, noise-induced signals on leads 24 that is inappropriately detected as intrinsic cardiac electrical activity may cause control module 40 or therapy module 44 to inhibit delivery of a desired pacing pulse and/or trigger delivery of an undesired pacing pulse.

IMD 22 operates in accordance with the sensing techniques of this disclosure to reduce the effect of EMI- or noise-induced signals on sensing and possibly pacing. Control module 40 may adjust a sensing threshold of sensing module 42 in response to detecting noise. Noise detection module 46 of IMD 22 may independently detect noise signals separately from the signals detected on one or both of leads 24a,b. To this end, noise detection module 46 may include a noise detection mechanism. Noise detection module 46 may, for example, receive noise signals by means of at least one antenna 58. In some instances, IMD 22 may include an antenna capable of detecting both RF fields and gradient magnetic fields. In other instances, IMD 22 may include one antenna for detecting the RF fields generated by MRI device 16 and another antenna (or other sensor) for detecting gradient magnetic fields generated by MRI device 16.

Antenna 58 of noise detection module 46 may be the same as antenna 56 of communication module 48, e.g., an inductive coil antenna, RF antenna or the like. For example, the signal received on antenna 56/58 may be divided and provided concurrently to communication module 48 and noise detection module 46. In another example, noise detection module 46 and communication module 48 may be a single module that analyzes the signals received on the antenna. Thus, noise signals that are induced in the telemetry antenna are detected and appropriately processed as described in further detail herein. In instances in which IMD 22 includes both an inductive coil antenna and an RF antenna, noise detection module 46 may be coupled to both.

In another example, antenna 58 may be at least one separate, dedicated antenna. One example antenna is described in U.S. Pat. No. 7,693,568 to Zeijlemaker, which is incorporated herein for its description of transducer 40 that detects MRI gradient magnetic fields. Transducer 40 of the '568 patent can detect an MRI gradient magnetic field via inductive coupling of the field with one of three orthogonal coils 41, 42, 43, depending upon the orientation of the field. Coils 41, 42, 43 of transducer 40 of the '568 patent are sensitive enough to detect small changes in the magnetic field, for example, between approximately 5 Tesla per second and approximately 300 Tesla per second. Again, the antenna of the '568 patent may be used in conjunction with another antenna that detects the RF signals.

In other instances, antenna 58 may be a different one of leads 24 than the lead on which the electrical signals are being monitored. For example, an atrial lead may be utilized as noise antenna for adjusting a sensing threshold associated with a sensing channel used to sense electrical signals on ventricular lead. In another example, antenna 58 may be a different sensing vector on the same lead on which the electrical signals are being monitored. In either of these cases, noise detection module 46 may be a part of the sensing module 42.

In response to detecting noise independently from the lead used to sense the desired cardiac electrical signals, control module 40 (or other module of IMD 22) determines the amplitude of the noise-induced signals on lead 24. Noise detection module 46 may, for example, analyze the electrical signals detected on the lead that coincide with the noise detected on antenna 58 to determine the amplitude of the noise-induced signals on lead 24. Control module 40 may include a peak detector that determines a peak amplitude of the noise-induced signals on lead 24 during a time period that coincides with noise detected on antenna 58. Control module 40 may use the measured amplitudes of the noise-induced signals on lead 24 to control adjustment of the sensing threshold of sensing module 42.

As described above, control module 40 may automatically adjust the sensing threshold of sensing module 42 in response to the output of noise detection module 46. Control module 40 may adjust the sensing threshold of sensing module 42 in response to detecting the first instance of noise by noise detection module 46. For example, control module 40 may adjust the sensing threshold immediately upon detecting the first instance of noise.

Control module 40 automatically adjusts the sensing threshold of sensing module 42 to a value capable of distinguishing between the cardiac signals and the noise signals induced on the lead by the RF fields and/or gradient magnetic fields. For noise-induced signals having amplitudes that are smaller than an amplitude of cardiac signals and adequately distinguishable from the cardiac signals, control module 40 may increase the sensing threshold to a value between the amplitude of the noise-induced signals and the amplitude of cardiac signals. In one example, control module 40 may increase the sensing threshold to a maximum sensing threshold value in response to noise detection module 46 detecting the first instance of noise. The maximum sensing threshold value may be predetermined or be determined as a function of one or more previously sensed cardiac signals. Increasing the sensing threshold may increase the accuracy of detecting intrinsic cardiac signals, even if the intrinsic cardiac signals occur at or near the same times as the noise signals. More accurate sensing may, in turn, improve pacing therapy provided during the MRI procedure.

In some instances, control module 40 may maintain the sensing threshold at the initially increased value until noise detection module 46 does not detect noise for a pre-defined period of time. In other instances, control module 40 may continue to adjust the sensing threshold over time. For example, control module 40 may gradually reduce the sensing threshold to a minimum increased threshold (e.g., to a value that is a certain percentage greater than the measured amplitude of the noise-induced signals on the lead or to a value halfway between the amplitude of the cardiac signal and the amplitude of the noise-induced signals on the lead). In another example, control module 40 may adjust the sensing threshold based on changes in the amplitude of subsequent noise signals or peaks of the subsequent noise signals (e.g., decrease the sensing threshold when the amplitude of the noise-induced signals on the lead decreases and increase the value of sensing threshold when the amplitude of the noise-induced signals on the lead increases).

In some cases, the noise-induced signals on the lead may have an amplitude that is too large to effectively distinguish from the intrinsic cardiac electrical signals, even with the increased sensing threshold. For example, the noise-induced signals on the lead may have an amplitude that is larger than the intrinsic cardiac electrical signals, in which case, increasing the sensing threshold would not result in the ability to distinguish the cardiac electrical signals from the noise signals. In this case, control module 40 may configure IMD 22 to operate in accordance with an MRI operating mode or other noise operating mode. In one example, control module 40 may configure IMD 22 to operate in an MRI operating mode that provides pacing therapy without relying on sensing, such as an asynchronous pacing mode. In another example, control module 40 may configure IMD 22 to operate in a pacing mode that triggers delivery of pacing therapy based on sensed electrical signals and independently detected noise. One such pacing mode is described in detail in co-pending patent application Ser. No. 13/095,076 to Ellingson et al., entitled, "PACING IN THE PRESENCE OF ELECTROMAGENTIC INTERFERENCE," which was filed on Apr. 27, 2011 and which is incorporated herein by reference in its entirety. The pacing mode described in the Ellingson et al. application delivers a pacing pulse subsequent to sensing an electrical signal on the lead when the sensed electrical signal coincides with an independently detected noise signal and the sensed electrical signal occurs during a period of time of an expected intrinsic cardiac signal.

Control module 40 may utilize the sensing threshold adjustment techniques of this disclosure during normal device operation. In other words, control module 40 may continually adjust sensing thresholds based on the independently detected noise. Alternatively, control module 40 may begin utilizing the sensing threshold adjustment techniques of this disclosure upon determining that IMD 22 is within an environment in which EMI is likely to be present, e.g., upon determining that IMD 22 is within environment 10 of FIG. 1. For example, IMD 22 may include one or more sensors, such as a magnetic field detector 52, which outputs a signal as a function of the magnetic field. Control module 40 (or magnetic field detector 52) may determine that IMD 22 is within environment 10 when the signal produced by magnetic field detector 52 is greater than or equal to a threshold level. Magnetic field detector 52 may, for example, be a Hall sensor or a reed switch.

In addition, control module 40 may temporarily suspend operation of other functionality of IMD 22 upon detecting environment 10 or MRI device 16. For example, control module 40 may disable tachycardia and fibrillation detection, high voltage therapy, impedance measurements, battery measurements, or the like. Prior to determining that IMD 22 is within environment 10, control module 40 may adjust the sensing threshold based on other automatic sensing adjustment algorithms, such as the technique described in U.S. Pat. No. 6,112,119 to Schuelke et al., which is incorporated herein by reference in its entirety.

The various modules of IMD 22 may include any one or more processors, controllers, digital signal processors (DSPs), application specific integrated circuits (ASICs), field-programmable gate arrays (FPGAs), or equivalent discrete or integrated circuitry, including analog circuitry, digital circuitry, or logic circuitry. Memory 50 may include computer-readable instructions that, when executed by control module 40 or other components of IMD 22, cause one or more components of IMD 22 to perform various functions attributed to those components in this disclosure. Memory 50 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other computer-readable storage media.

Figure 4:
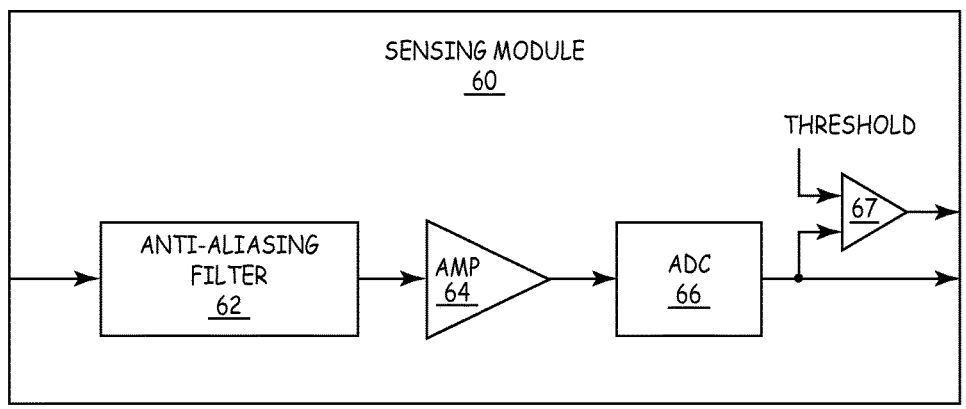
FIG. 4 is a functional block diagram illustrating components of an example sensing module of an IMD.

FIG. 4 is a functional block diagram illustrating components of an example sensing module 60. Sensing module 60 may correspond with sensing module 42 of FIG. 3. Sensing module 60 includes an anti-aliasing filter 62, an amplifier 64, an ADC 66, and a threshold detector 67. Sensing module 62 may include other components in addition to or instead of those illustrated in FIG. 4, such as a rectifier, digital signal processor or other components to process the sensed signal. As such, sensing module 60 of FIG. 4 is presented for illustrative purposes only, and is not intended to limit the scope of the present disclosure.

The components illustrated in FIG. 4 may form a first sensing channel of sensing module 60. The sensing channel processes the sensed signal and provides the processed signal or a result obtained from processing the sensed signal (e.g., existence of a P- or R-wave) to control module 40. The first sensing channel may, for example, process signals sensed by electrodes 28a and 30a of lead 24a. As described above, however, sensing module 60 may have more than one sensing channel, such as a sensing channel for an atrial electrical signal and a sensing channel for a ventricular electrical signal. In this case, sensing module 60 may include additional components forming additional sensing channels. The multiple sensing channels may share one or more components or may have their own separate components.

Anti-aliasing filter 62 of sensing module 60 receives a signal sensed by one or more electrodes 28a,b and 30a,b and filters the signal. Anti-aliasing filter 62 restricts the bandwidth of the signal that will be provided to amplifier 64 and ADC 66. Amplifier 64 obtains the filtered signal from anti-aliasing filter 62 and amplifies the signal. Amplifier 64 may, for example, have a gain between several tens to several hundreds for amplifying cardiac electrical signals. This range of gains is exemplary and should not be considered limiting of the disclosure. Amplifier 64 may have larger or smaller gains. ADC 66 receives the amplified signal and converts the signal to a digital format for subsequent signal processing.

The output of ADC 66 is provided to threshold detector 67. Threshold detector 67 compares the output of the ADC 66 to a threshold value (labeled "THRESHOLD" in FIG. 4). Threshold detector 67 determines whether the signal exceeds the threshold value. In one example, threshold detector 67 may be a comparator. When the signal exceeds the threshold value, threshold detector 67 indicates that a cardiac event (e.g., a P-wave or R-wave) has occurred. The output of ADC 66 may, in some instances, be divided and provided directly to control module 40 in parallel with threshold detector 67.

The signal received by sensing module 60 includes cardiac electrical signals and any noise signal induced on leads 24, including noise signals induced by external field 18. In instances in which the noise signal induced on leads 24 is greater than the threshold provided to threshold detector 67, sensing module 60 may detect the noise signal as a cardiac electrical signal. Inappropriately detecting the noise signals as cardiac signals may have undesirable effects on the pacing therapy provided by therapy module 44, particularly when therapy module 44 delivers the pacing therapy as a function of the sensed electrical signals on leads 24. For example, detecting the noise signals on leads 24 as cardiac electrical signals may cause control module 40 or therapy module 44 to inhibit delivery of a desired pacing pulse and/or trigger delivery of an undesired pacing pulse. Control module 40 may adjust the threshold provided to threshold detection module 67 in accordance with the techniques described in this disclosure.

Figure 5:
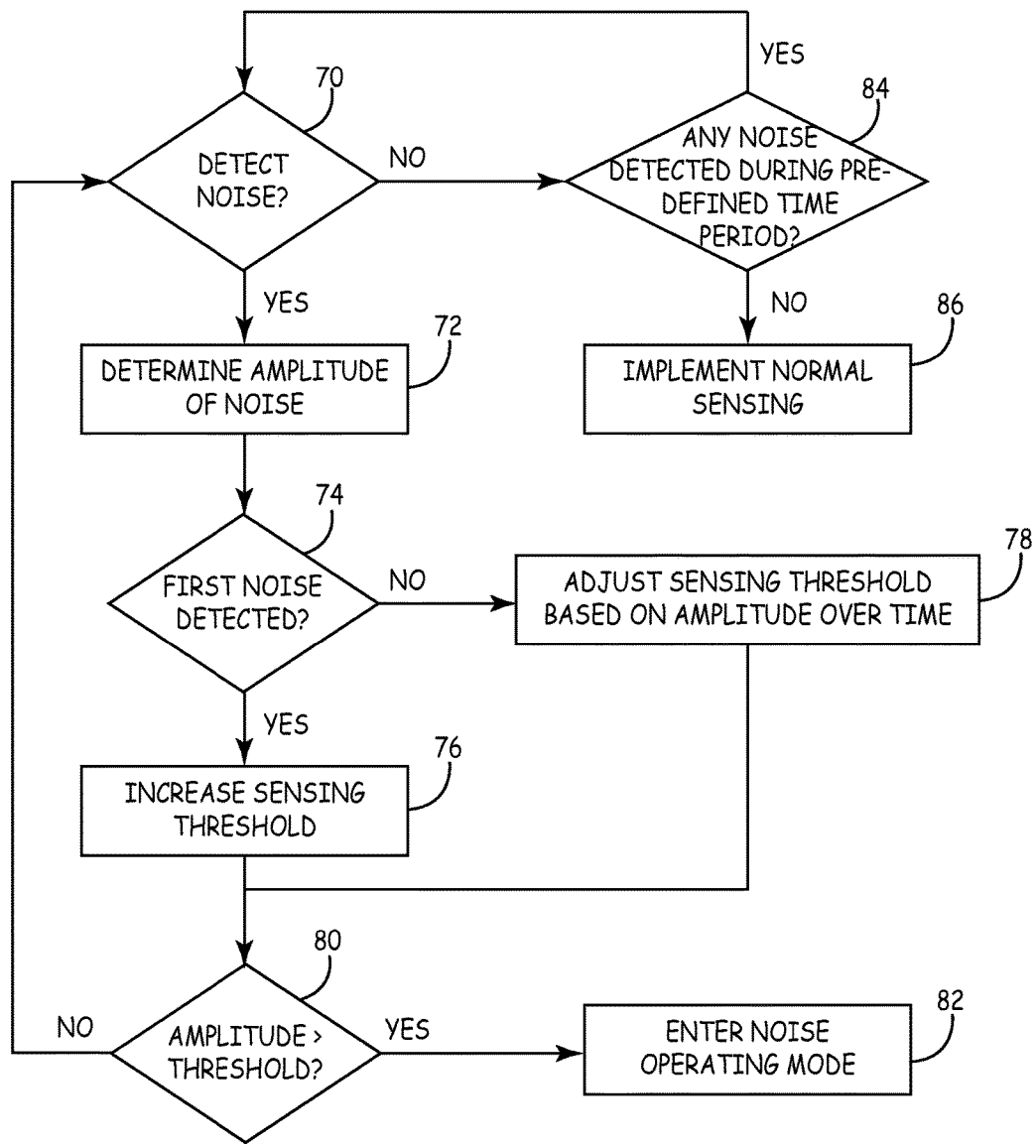
FIG. 5 is a flow diagram illustrating an example operation of an IMD adjusting a sensing threshold in accordance with the techniques of this disclosure.

FIG. 5 is a flow diagram illustrating an example operation of an IMD, such as IMD 22, adjusting a sensing threshold in accordance with the techniques of this disclosure. IMD 22 determines whether noise is detected on antenna 58 (70). Control module 40 may, for example, analyze an output of noise detection module 46 to determine whether noise is detected on antenna 58. When control module 40 detects noise ("YES" branch of block 70), control module 40 determines an amplitude of the noise-induced signals on the lead (72). Control module 40 may, for example, analyze the portion of the electrical signals sensed on the lead during a period of time corresponding to noise detected on antenna 58. The period of time analyzed to determine the amplitude of the noise-induced signals on the lead is therefore confirmed as being noise via an independent source (e.g., antenna 58).

Control module 40 determines whether the noise signal is the first noise signal detected within a predetermined period of time (74). The predetermined period of time may be selected to be a duration during which at least one noise signal would likely be received in a noisy environment. In one example, the predetermined period of time may be around ten minutes. However, the predetermined period of time may be greater than or less than ten minutes.

When control module 40 determines that the noise signal is the first noise signal detected within the predetermined period of time ("YES" branch of block 74), control module 40 increases the sensing threshold (76). In one example, control module 40 increases the sensing threshold to a maximum threshold value at which the cardiac electrical signals can be accurately sensed. The maximum threshold value may, for instance, be equal to seventy-five percent of the amplitude of the last sensed cardiac electrical signal, the last sensed cardiac electrical signal before the first noise signal is detected, or an average amplitude of a plurality of sensed cardiac electrical signals.

When control module 40 determines that the noise signal is not the first noise signal detected within the predetermined period of time ("NO" branch of block 74), control module 40 may further adjust the sensing threshold based on amplitude changes of the noise signals over time (78). Control module 40 may, for example, gradually decrease the sensing threshold from the previous threshold value to a minimum increased threshold value (e.g., to a value that is a certain percentage greater than the amplitude of one or more of the noise-induced signals on the lead or to a value halfway between the amplitude of the cardiac signals and the amplitude of the noise-induced signals on the lead). In other instances, control module 40 may keep the sensing threshold at the initially increased value.

After adjusting the sensing threshold (e.g., at either block 76 or block 78), control module 40 compares the amplitude of the noise-induced signal(s) with a threshold amplitude (80). For the first noise-induced signal, control module 40 may compare the amplitude of the first noise-induced signal to the threshold amplitude. For subsequent noise-induced signals, control module 40 may compare an average amplitude of a plurality of noise-induced signals to the threshold amplitude. The threshold amplitude may be a maximum amplitude that is capable of accurately distinguishing noise signals from cardiac electrical signals. In some instances, the threshold amplitude may be equal to a percentage of the amplitude of one or more sensed cardiac electrical signals.

For example, the threshold amplitude may be equal to approximately seventy-five (75) percent of the one or more sensed cardiac electrical signals. The threshold amplitude may be equal to a percentage of the last sensed cardiac electrical signal or an average amplitude of a plurality of sensed cardiac electrical signals. Because the noise signal will also be superimposed on the electrical signals sensed on lead 24, control module 40 may utilize the last sensed cardiac electrical signal before the first noise signal is detected, or an average amplitude of a plurality of sensed cardiac electrical signals to determine the threshold amplitude.

When control module 40 determines that the amplitude of the noise-induced signal(s) is greater than the threshold amplitude ("YES" branch of block 80), control module 40 transitions operation of IMD 22 into a noise operating mode (82). Control module 40 may, for example, configure IMD 22 to operate in a noise operating mode that provides pacing therapy without relying on sensing, such as an asynchronous pacing mode, in response to determining that the amplitude of the noise-induced signal(s) on the lead is greater than the threshold amplitude. In another example, control module 40 may configure IMD 22 to operate in a pacing mode that triggers a pacing pulse subsequent to sensing an electrical signal on the lead when the sensed electrical signal coincides with an independently detected noise signal and the sensed electrical signal occurs during a period of time of an expected intrinsic cardiac signal, e.g., as described in Ellingson et al. (referenced above).

When control module 40 determines that the amplitude of the noise-induced signal(s) is not greater than the threshold amplitude ("NO" branch of block 80), IMD 22 continues to monitor for noise on antenna 58 or other detection mechanism at block 70. When no noise is detected on antenna 58 or other detection mechanism ("NO" branch of block 70), control module 40 determines whether any noise has been detected during the predetermined period of time (84). Again, the predetermined period of time may be selected to be a duration during which at least one noise signal would likely be received in a noisy environment. In one example, the predetermined period of time may be around ten minutes. However, the predetermined period of time may be greater than or less than ten minutes. When any noise has been detected during the predetermined period of time ("YES" branch of block 84), IMD 22 continues to monitor for noise on antenna 58 or other detection mechanism at block 70. When no noise has been detected during the predetermined period of time ("NO" branch of block 84), control module 40 operates IMD 22 in the normal sensing mode, e.g., using the sensing threshold prior to detection of the noise (86). The sensing threshold adjustment techniques may increase the accuracy of detecting intrinsic cardiac signals, even if the intrinsic cardiac signals occur at or near the same times as the MRI-induced noise signals, thereby improving therapy during an MRI scan or in another noisy environment.

Figure 6:
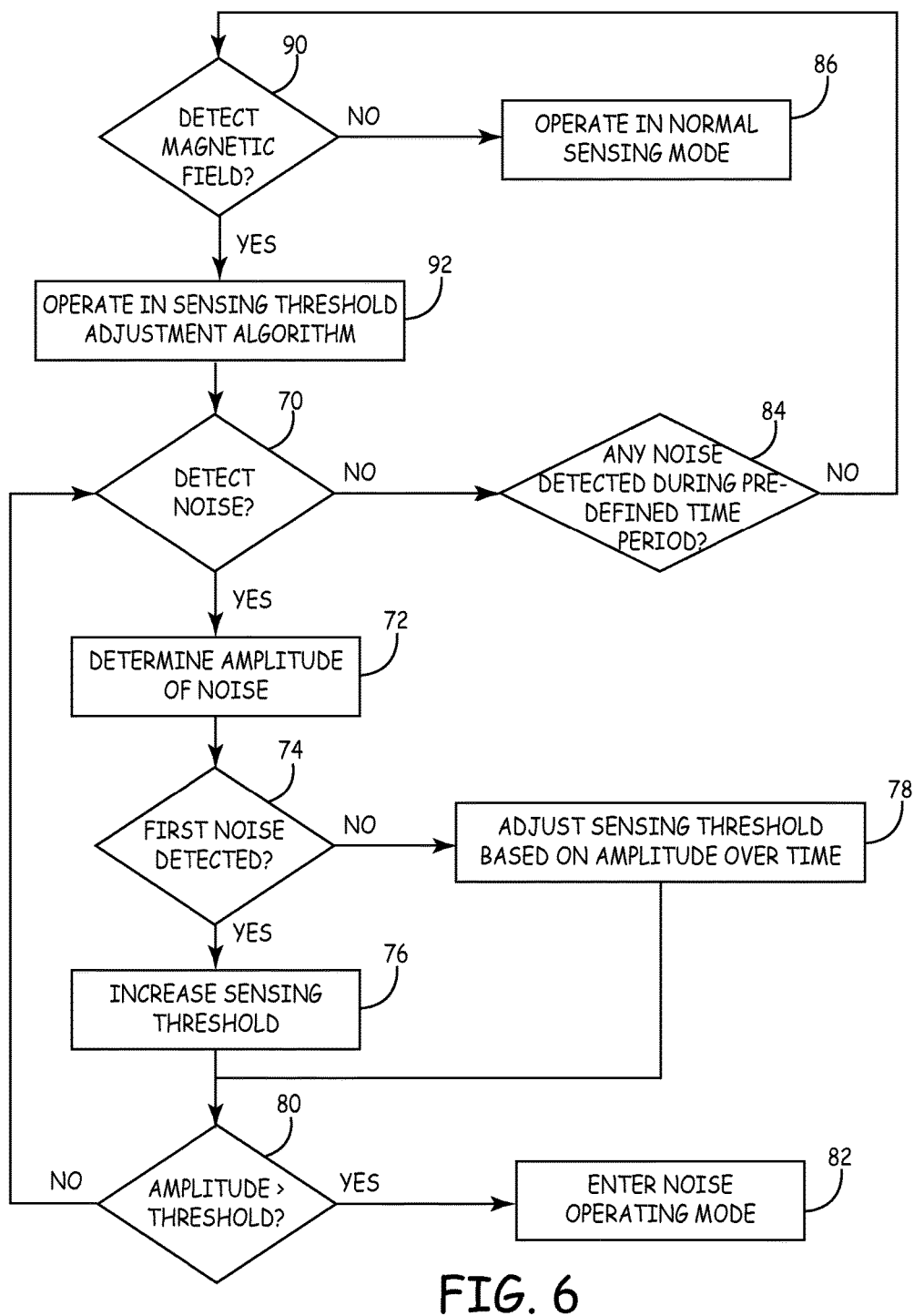
FIG. 6 is a flow diagram illustrating another example operation of an IMD adjusting a sensing threshold in accordance with the techniques of this disclosure.

FIG. 6 is a flow diagram illustrating another example operation of an IMD, such as IMD 22, adjusting a sensing threshold in accordance with the techniques of this disclosure. Control module 40 determines whether a magnetic field having particular characteristics is detected (90). Control module 40 may analyze an output of magnetic field detector 52 to determine whether a magnetic field having a strength larger than a threshold strength has been detected. When control module 40 detects the magnetic field having particular characteristics ("YES" branch of block 90), control module 40 initiates the sensing threshold adjustment techniques of this disclosure (92). Additionally, control module 40 may temporarily suspend operation of other functionality of IMD 22 upon detecting the magnetic field having particular characteristics. For example, control module 40 may suspend tachycardia and fibrillation detection, high voltage therapy, impedance measurements, battery measurements, or the like.

IMD 22 monitors for noise on antenna 58 or other detection mechanism (70). Blocks 70-84 are described in detail with respect to FIG. 5 and will not be repeated here. When no noise has been detected during the predetermined period of time ("NO" branch of block 84), control module 40 determines whether the magnetic field having particular characteristics is detected (90). When no magnetic field having particular characteristics is detected ("NO" branch of block 90), control module 40 operates IMD 22 in the normal sensing mode, e.g., using the sensing threshold prior to detection of the noise (86). In this manner, control module 40 may begin utilizing the sensing threshold adjustment techniques of this disclosure upon determining that IMD 22 is within an environment in which noise is likely to be present, e.g., upon determining that IMD 22 is within environment 10 of FIG. 1.

FIGS. 7-10 illustrate timing diagrams demonstrating example operation of an IMD implementing the techniques of this disclosure. The amplitudes, frequencies, and sensing threshold changes of FIGS. 7-10 are provided for illustrative purposes only and should not be considered limiting of the techniques described herein.

Figure 7:
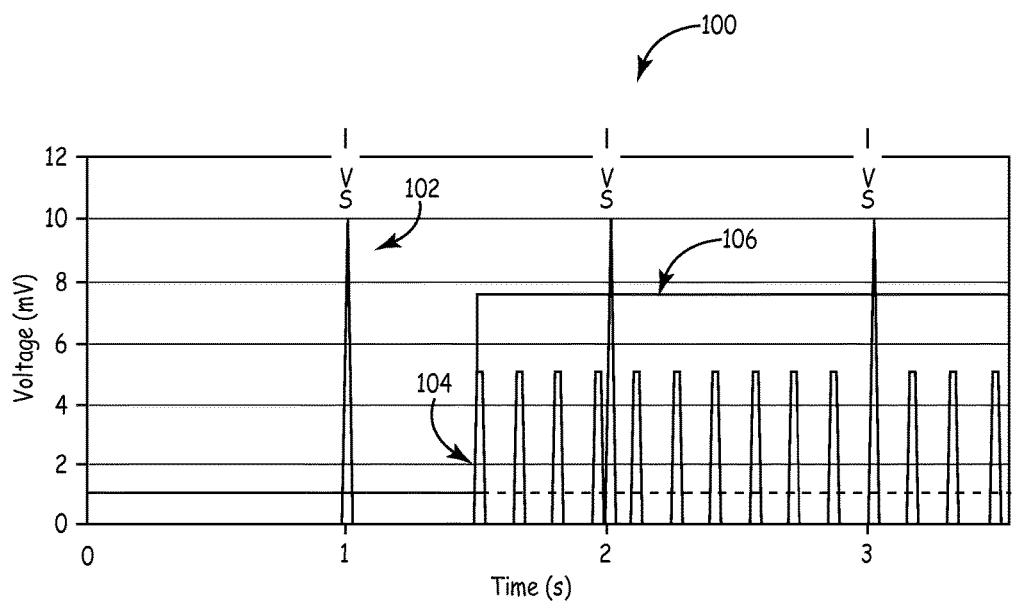
FIGS. 7-10 illustrate timing diagrams demonstrating example operation of an IMD implementing the techniques of this disclosure.

FIG. 7 illustrates a timing diagram 100. Timing diagram 100 shows a cardiac electrical signal on a lead (labeled 102), a noise-induced signal on the lead (labeled 104), and a sensing threshold of sensing circuit (labeled 106). Although noise-induced signal 104 would be superimposed on cardiac electrical signal 102 as both are received on lead 24, the two signals are shown independently for purposes of illustration. In the timing diagram 100 illustrated in FIG. 7, the patient has a current heart rate of 60 beats per minute as illustrated in the cardiac electrical signal 102 having spikes occurring at 1 second, 2 seconds and 3 seconds corresponding to depolarizations. The spikes corresponding to depolarizations have amplitudes equal to approximately 10 millivolts (mV).

Noise-induced signal 104 begins at approximately the 1.5 second time frame in the timing diagram of FIG. 7. Noise-induced signal 104 may, for example, correspond with the beginning of an MRI procedure and correspond to either the RF signals or the gradient magnetic fields of MRI device 16. The amplitude of the spikes of noise-induced signal 104 are approximately 5 mV, which is above the original sensing threshold of approximately 1 mV. As such, if the sensing threshold remained unchanged, each of the spikes of noise signal 104 would be detected as cardiac electrical signals by sensing module 42.

As described in detail herein, IMD 22 includes a noise detection module 46 that detects the noise signal independently of lead 24. The noise signal detected independently of lead 24 is not illustrated in FIG. 7, but would have spikes corresponding to each of the spikes of noise-induced signal on lead 24 (labeled 104). Control module 40 adjusts the sensing threshold upon noise detection module 46 detecting a first instance of noise independently of lead 24, e.g., on antenna 58. In some instances, the sensing threshold is adjusted almost immediately after detecting the noise.

Control module 40 increases sensing threshold 106 to a value between the amplitude of noise-induced signal 104 on the lead (e.g., 5 mV in this example) and the amplitude of the cardiac electrical signal (e.g., 10 mV in this example). In the example illustrated in the timing diagram of FIG. 7, control module 40 increases sensing threshold 106 from 1 mV to approximately 7.5 mV, which is approximately equal to seventy-five (75) percent of the amplitude of the cardiac electrical signal. However, control module 40 may increase the sensing threshold to other amounts, e.g., based on the amplitude of the cardiac electrical signal, the amplitude of the noise-induced signal on the lead or both.

Using the increased sensing threshold, control module 40 can now detect the spikes in cardiac electrical signal 102 without detecting the spikes in noise-induced signal 104. This allows for increased accuracy detecting the intrinsic cardiac events, even if the intrinsic cardiac events occur at or near the same time as the peaks of noise-induced signal 104. Sensing threshold 106 remains at the increased value until control module 40 reverts back to the normal sensing threshold (e.g., in response to not detecting noise for a predetermined period of time).

Figure 8:
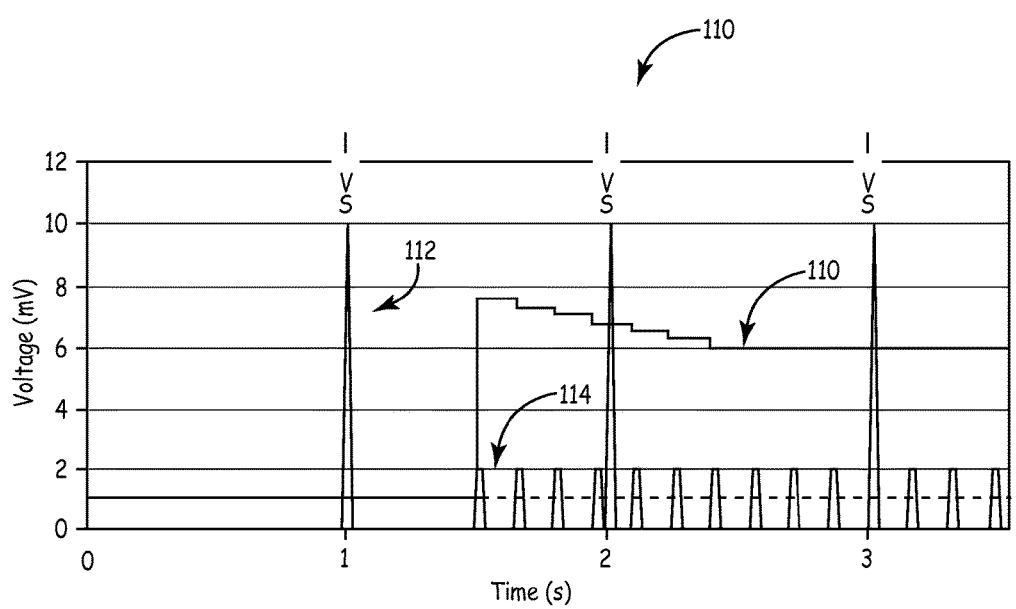

FIG. 8 illustrates a timing diagram 110. Timing diagram 110 shows a cardiac electrical signal on lead 24 (labeled 112), a noise-induced signal on lead 24 (labeled 114), and a sensing threshold of sensing circuit (labeled 116). Although noise-induced signal 114 would be superimposed on cardiac electrical signal 112 as both are received on lead 24, the two signals are shown independently for purposes of illustration. In the timing diagram 110 illustrated in FIG. 8, the patient again has a current heart rate of 60 beats per second as illustrated in the cardiac electrical signal 112 having spikes occurring at approximately 1 second, 2 seconds and 3 seconds corresponding to depolarizations. The spikes corresponding to depolarizations have amplitudes equal to approximately 10 millivolts (mV).

Noise-induced signal 114 begins at approximately the 1.5 second time frame in the timing diagram of FIG. 8. Noise-induced signal 114 may, for example, correspond with the beginning of an MRI procedure and correspond to either the RF signals or the gradient magnetic fields of MRI device 16. The amplitude of the spikes of noise-induced signal 114 are approximately 2 mV, which is above the original sensing threshold of approximately 1 mV. As such, if the sensing threshold remained unchanged, each of the spikes of noise-induced signal 114 would be detected as cardiac electrical signals by sensing module 42.

In accordance with the techniques of this disclosure, control module 40 adjusts the sensing threshold upon detecting a first instance of noise independently of lead 24, e.g., on antenna 58. The noise signal detected independently of lead 24 is not illustrated in FIG. 8, but would have spikes corresponding to each of the spikes of noise-induced signal 114. As such, the first instance of noise that is independently detected would correspond with the first spike of noise-induced signal 114. In some instances, the sensing threshold is adjusted almost immediately after detecting the first instance of noise.

Control module 40 increases sensing threshold 116 to a value between the amplitude of noise-induced signal 114 (e.g., 2 mV in this example) and the amplitude of the cardiac electrical signal (e.g., 10 mV in this example). In the example illustrated in the timing diagram of FIG. 8, control module 40 increases sensing threshold 116 from approximately 1 mV to approximately 7.5 mV in response to detecting the first peak of noise-induced signal 114. However, control module 40 may increase the sensing threshold to other amounts, e.g., based on the amplitude of the cardiac electrical signal, the amplitude of the noise-induced signal or both.

Using the increased sensing threshold, control module 40 can now detect the spikes in cardiac electrical signal 112 without detecting the spikes in noise-induced signal 114. This allows for increased accuracy detecting the intrinsic cardiac events, even if the intrinsic cardiac events occur at or near the same time as the peaks of noise-induced signal 114. Unlike sensing threshold 106 of timing diagram 100 of FIG. 7, sensing threshold 116 does not remain at the initially increased value. Instead, control module 40 continues to adjust the sensing threshold 116 over time. Control module 40 may, for example, gradually decrease sensing threshold 116 from the initial value to a minimum allowable increased value (e.g., 6 mV in the illustrated example). The minimum allowable increased value may be a value that is a certain percentage greater than the amplitude of each spike of noise-induced signal 114 or an average amplitude of a plurality the spikes of noise-induced signal 114, or the minimum allowable increased value may be a value halfway between the amplitude of the cardiac electrical signal and the amplitude of the latest spike of noise-induced signal 114 or an average amplitude of a plurality the spikes of noise-induced signal 114. The sensing threshold remains at the minimum allowable increased value until control module 40 reverts back to the normal sensing threshold (e.g., in response to not detecting noise for a predetermined period of time) or the amplitude of noise-induced signal 114 changes at which point a new adjusted sensing threshold may be set. Control module 40 may also adjust the sensing threshold 116 based on amplitude changes of the cardiac electrical signal 112 over time in addition to the adjustments made based on amplitude changes of noise-induced signal 114.

Figure 9:
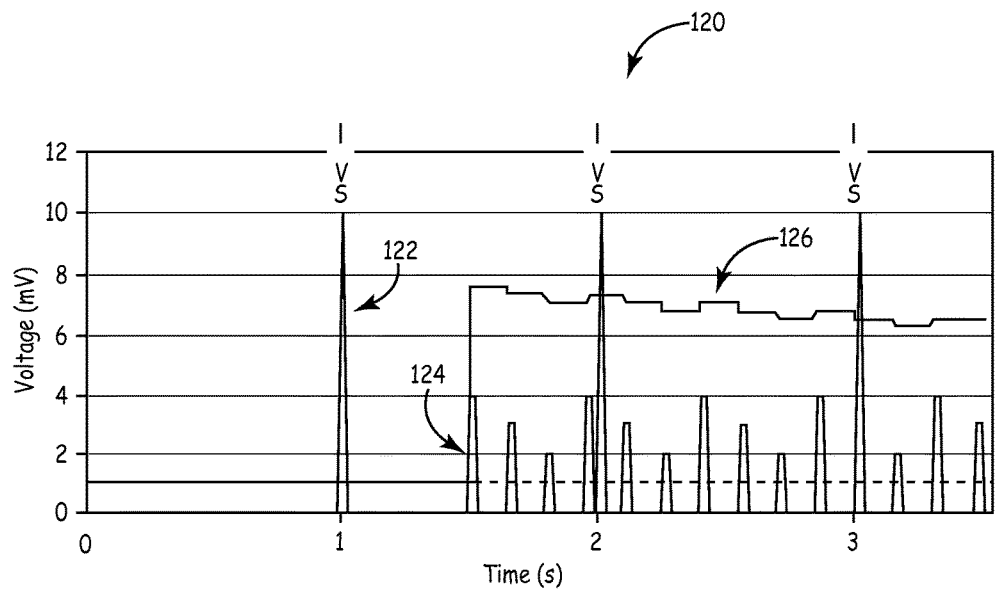

FIG. 9 illustrates a timing diagram 120. Timing diagram 120 shows a cardiac electrical signal (labeled 122), a noise-induced signal (labeled 124), and a sensing threshold of sensing circuit (labeled 126). Although noise-induced signal 124 would be superimposed on cardiac electrical signal 122 as both are received on lead 24, the two signals are shown independently for purposes of illustration. In the timing diagram 120 illustrated in FIG. 9, the patient again has a current heart rate of 60 beats per second as illustrated in the cardiac electrical signal 122 having spikes occurring at approximately 1 second, 2 seconds and 3 seconds corresponding to depolarizations. The spikes corresponding to depolarizations have amplitudes equal to approximately 10 millivolts (mV).

Noise-induced signal 124 begins at approximately the 1.5 second time frame in the timing diagram of FIG. 9. Noise-induced signal 124 may, for example, correspond with the beginning of an MRI procedure and correspond to either the RF signals or the gradient magnetic fields of MRI device 16. The amplitude of the spikes of noise-induced signal 124 range from approximately 4 mV to approximately 2 mV, which is above the original sensing threshold of approximately 1 mV. As such, if the sensing threshold remained unchanged, each of the spikes of noise-induced signal 124 would be detected as cardiac electrical signals by sensing module 42.

In accordance with the techniques of this disclosure, control module 40 adjusts the sensing threshold upon detecting a first instance of noise independently of lead 24, e.g., on antenna 58. The noise signal detected independently of lead 24 is not illustrated in FIG. 8, but would have spikes corresponding to each of the spikes of noise-induced signal 124. As such, the first instance of noise that is independently detected would correspond with the first spike of noise-induced signal 124. In some instances, the sensing threshold is adjusted almost immediately after detecting the first instance of noise.

Control module 40 increases sensing threshold 126 to a value between the amplitude of the first spike of noise-induced signal 124 (e.g., 4 mV in this example) and the amplitude of the cardiac electrical signal (e.g., 10 mV in this example). In the example illustrated in the timing diagram of FIG. 9, control module 40 increases sensing threshold 126 from approximately 1 mV to approximately 7.5 mV in response to detecting the first peak of noise-induced signal 124. However, control module 40 may increase the sensing threshold to other amounts, e.g., based on the amplitude of the cardiac electrical signal, the amplitude of the noise-induced signal or both.

Using the increased sensing threshold, control module 40 can now detect the spikes in cardiac electrical signal 122 without detecting the spikes in noise-induced signal 124. This allows for increased accuracy detecting the intrinsic cardiac events, even if the intrinsic cardiac events occur at or near the same time as the peaks of noise-induced signal 124. Like sensing threshold 116 of timing diagram 110 of FIG. 8, control module 40 continues to adjust the sensing threshold 126 over time. In the example illustrated in FIG. 9, control module 40 adjusts sensing threshold 126 based on changes in amplitude of the peaks of noise-induced signal 124 subsequent to the first peak. When the amplitude of noise-induced signal decreases, control module 40 decreases the value of sensing threshold 126. Likewise, when the amplitude of noise-induced signal increase, control module 40 increases the value of sensing threshold 126. The increases and decreases in sensing threshold 126 over time may occur at predetermined increments or steps, e.g., steps of 0.25 mV or other increments. Alternatively, the increases and decreases in sensing threshold 126 may be determined as a function of the amplitude of the noise-induced signal.

Like sensing threshold 116 of timing diagram 110 of FIG. 8, the sensing threshold 126 may ultimately converge on a minimum allowable increased value (e.g., 6 mV). The minimum allowable increased value may be a value that is a certain percentage greater than the amplitude of each spike of noise-induced signal 114 or an average amplitude of a plurality the spikes of noise-induced signal 114, or the minimum allowable increased value may be a value halfway between the amplitude of the cardiac electrical signal and the amplitude of the latest spike of noise-induced signal 114 or an average amplitude of a plurality the spikes of noise-induced signal 114. Control module 40 reverts back to the normal sensing threshold (e.g., in response to not detecting noise for a predetermined period of time). Control module 40 may also adjust the sensing threshold 126 based on amplitude changes of the cardiac electrical signal 122 over time in addition to the adjustments made based on amplitude changes of noise-induced signal 124.

Figure 10:
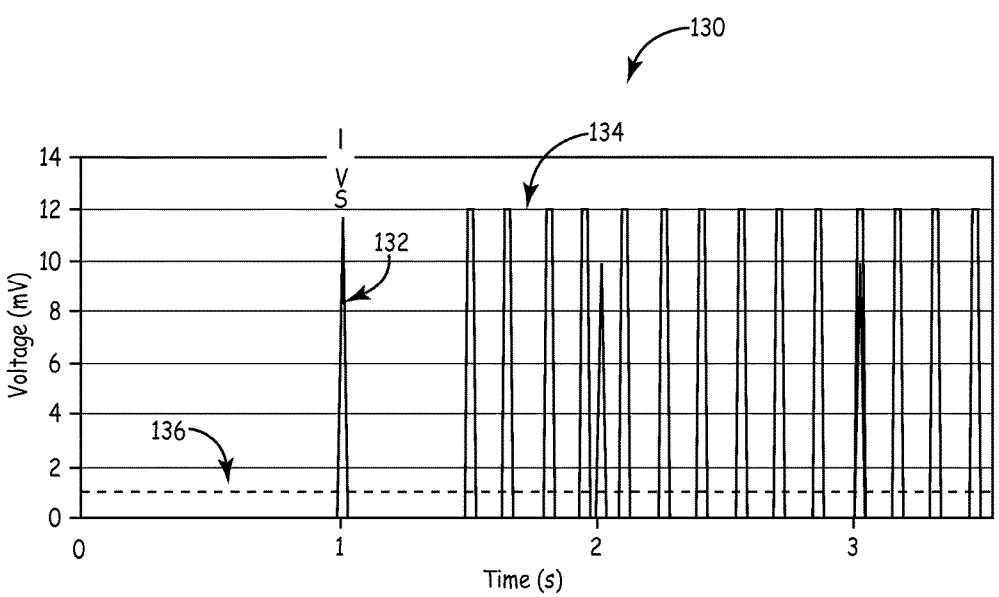

FIG. 10 illustrates a timing diagram 130. Timing diagram 130 shows a cardiac electrical signal (labeled 132), a noise-induced signal (labeled 134), and a sensing threshold of sensing circuit (labeled 136). Although noise-induced signal 134 would be superimposed on cardiac electrical signal 132 as both are received on lead 24, the two signals are shown independently for purposes of illustration. In the timing diagram 130 illustrated in FIG. 10, the patient again has a current heart rate of 60 beats per second as illustrated in the cardiac electrical signal 132 having spikes occurring at approximately 1 second, 2 seconds and 3 seconds corresponding to depolarizations. The spikes corresponding to depolarizations have amplitudes equal to approximately 10 millivolts (mV).

Noise-induced signal 134 begins at approximately the 1.5 second time frame in the timing diagram of FIG. 10. Noise-induced signal 134 may, for example, correspond with the beginning of an MRI procedure and correspond to either the RF signals or the gradient magnetic fields of MRI device 16. The amplitude of the spikes of noise-induced signal 134 are approximately 12 mV, which is above the amplitude of spikes of the cardiac electrical signal 132. As such, even if the sensing threshold was increased, control module 40 would be unable to accurately distinguish cardiac electrical signal 132 from noise-induced signal 134. In some instances, control module 40 may actually increase the sensing threshold upon detecting the first instance of noise independent of the signals on the lead and revert back to the normal sensing threshold upon determining that the amplitude of the noise-induced signal is greater than the cardiac electrical signals (or a threshold amplitude).

Instead, control module 40 transitions IMD to a noise operating mode. In one example, control module 40 configures IMD 22 to operate in a noise operating mode that provides pacing therapy without relying on sensing, such as an asynchronous pacing mode. In another example, control module 40 configures IMD 22 to operate in a pacing mode that triggers a pacing pulse subsequent to sensing an electrical signal on the lead when the sensed electrical signal coincides with an independently detected noise-induced signal and the sensed electrical signal occurs during a period of time of an expected intrinsic cardiac signal, e.g., as described in Ellingson et al. (referenced above).

In other instances, control module 40 may not adjust sensing threshold 136 even when the amplitude of noise-induced signal 134 is not larger than the amplitude of cardiac electrical signal 132. For example, control module 40 may not adjust sensing threshold 136 if the amplitude of noise-induced signal 134 is smaller than the amplitude of cardiac electrical signal 132, but close enough to cardiac electrical signal 132 to be unable to accurately distinguish the two.

The techniques described in this disclosure, including those attributed to one or more components of IMD 22, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, SRAM, EEPROM, flash memory, magnetic data storage media, optical data storage media, or the like. The instructions may be executed to support one or more aspects of the functionality described in this disclosure.

Various examples have been described. These and other examples are within the scope of the following claims.

The invention claimed is:

1. An implantable medical system comprising:
an implantable medical lead including at least one electrode;
an implantable medical device coupled to the implantable medical lead, the implantable medical device comprising:
a sensing module configured to obtain electrical signals using a sensing vector that includes the at least one electrode of the implantable medical lead, wherein the electrical signals include cardiac signals and noise-induced signals;
a noise detection module configured to independently obtain noise signals without using the sensing vector that includes the at least one electrode of the implantable medical lead;
a magnetic field detector that provides an output that is a function of a strength of a magnetic field to which the implantable medical device is exposed; and
a control module configured to adjust a sensing threshold of the sensing module to a value between an amplitude of the noise-induced signals and an amplitude of the cardiac signals in response to the detection of at least one of the noise signals independently of the electrical signals obtained using the sensing vector that includes the at least one electrode and determination that the output of the magnetic field detector exceeds a threshold.

2. The system of claim 1, wherein the control module is configured to adjust the sensing threshold in response to detecting a first one of the noise signals on the noise detection module.

3. The system of claim 1, wherein the control module is configured to adjust the sensing threshold as a function of the amplitude of one or more noise-induced signals obtained via the sensing module.

4. The system of claim 3, wherein the control module is configured to adjust the sensing threshold based on the amplitude of each noise-induced electrical signal obtained via the sensing module.

5. The system of claim 1, wherein the control module is configured to determine that no noise signals have been detected via the noise detection module for a predetermined period of time and resets the sensing threshold to a value corresponding to the value used prior to detecting the noise signals.

6. The system of claim 1, wherein the magnetic field detector comprises one of a Hall effect sensor and reed switch.

7. The system of claim 1, further comprising an antenna coupled to the noise detection module, wherein the antenna is dedicated to receiving noise signals.

8. The system of claim 1, further comprising an antenna coupled to the noise detection module, wherein the antenna is a telemetry antenna configured to receive telemetry communication signals from a second device.

9. The system of claim 1, wherein the implantable medical lead comprises a first implantable medical lead, the system further comprising a second implantable medical lead that includes at least one electrode, wherein the noise detection module is configured to obtain the noise signals on the second implantable medical lead.

10. The system of claim 1, wherein the implantable medical lead includes a plurality of electrodes and the noise detection module is configured to obtain the noise signals using a second sensing vector that is different than the sensing vector used to obtain electrical signals for the sensing module.

11. An implantable medical system comprising:
an implantable medical lead including at least one electrode;
an implantable medical device coupled to the implantable medical lead, the implantable medical device comprising:
a sensing module configured to obtain electrical signals using a sensing vector that includes the at least one electrode of the implantable medical lead, wherein the electrical signals include cardiac signals and noise-induced signals;
a noise detection module configured to independently obtain noise signals without using the sensing vector that includes the at least one electrode of the implantable medical lead;
a control module configured to adjust a sensing threshold of the sensing module to a value between an amplitude of the noise-induced signals and an amplitude of the cardiac signals in response to the detection of at least one of the noise signals independently of the electrical signals obtained using the sensing vector that includes the at least one electrode,
wherein the control module is configured to compare the amplitude of the noise-induced electrical signals obtained using the sensing vector that includes the at least one electrode of implantable medical lead to a threshold noise amplitude, transition to a noise operating mode when the amplitude of at least one of the noise-induced electrical signals exceeds the threshold noise amplitude, and adjust the sensing threshold of the sensing module when the amplitude of at least one of the noise-induced electrical signals does not exceed the threshold noise amplitude.

12. The system of claim 11, wherein the threshold noise amplitude is one of a percentage of the amplitude of a previously sensed electrical signal on the implantable medical lead or an average amplitude of a plurality of previously sensed electrical signals on the implantable medical lead.

13. The system of claim 11, wherein the noise operating mode is an asynchronous pacing mode.

14. The system of claim 11, wherein the noise operating mode is a non-pacing mode.

15. A method comprising:
sensing electrical signals using a sensing vector that includes at least one electrode on an implantable medical lead, wherein the electrical signals include cardiac signals and noise-induced signals;
independently sensing noise signals without using the sensing vector that includes the at least one electrode on the implantable medical lead;
determining that a magnetic field to which the implantable medical device is exposed exceeds a threshold strength; and
adjusting a sensing threshold used to sense the electrical signals of the implantable medical lead to a value between an amplitude of one or more of the noise-induced signals and an amplitude of the cardiac electrical signals in response to sensing at least one of the noise signals independently of the electrical signals sensed using the sensing vector that includes the at least one electrode on the implantable medical lead and determining that the magnetic field exceeds the threshold strength.

16. The method of claim 15, wherein adjusting the sensing threshold comprises adjusting the sensing threshold in response to sensing a first one of the noise signals independently of the electrical signals sensed using the sensing vector that includes the at least one electrode on the implantable medical lead.

17. The method of claim 15, further comprising adjusting the sensing threshold as a function of the amplitude of one or more of the noise-induced signals sensed on the implantable medical lead.

18. The method of claim 17, wherein adjusting the sensing threshold comprises adjusting the sensing threshold based on the amplitude of each noise-induced electrical signal on the implantable medical lead.

19. The method of claim 15, further comprising:
determining that no noise signals have been detected independently of the electrical signals sensed using the sensing vector that includes the at least one electrode on the implantable medical lead for a predetermined period of time; and
resetting the sensing threshold to a value corresponding to the value used prior to detecting the noise signals.

20. A method comprising:
sensing electrical signals using a sensing vector that includes at least one electrode on an implantable medical lead, wherein the electrical signals include cardiac signals and noise-induced signals;
independently sensing noise signals without using the sensing vector that includes the at least one electrode on the implantable medical lead;
adjusting a sensing threshold used to sense the electrical signals of the implantable medical lead to a value between an amplitude of one or more of the noise-induced signals and an amplitude of the cardiac electrical signals in response to sensing at least one of the noise signals independently of the electrical signals sensed using the sensing vector that includes the at least one electrode on the implantable medical lead;
comparing an amplitude of the noise-induced electrical signals sensed using the sensing vector that includes the at least one electrode on the implantable medical lead to a threshold noise amplitude;
transitioning to a noise operating mode when the amplitude of at least one of the noise-induced electrical signals exceeds the threshold noise amplitude; and
adjusting the sensing threshold of the sensing module when the amplitude of at least one of the noise-induced electrical signals does not exceed the threshold noise amplitude.

21. A non-transitory computer-readable medium comprising instructions that, when executed, cause an implantable medical device to:
sense electrical signals using a sensing vector that includes at least one electrode on an implantable medical lead, wherein the electrical signals include cardiac signals and noise-induced signals;
independently sense noise signals without using the sensing vector that includes the at least one electrode on the implantable medical lead;
determine that a magnetic field to which the implantable medical device is exposed exceeds a threshold strength; and
adjust a sensing threshold used to sense the electrical signals of the implantable medical lead to a value between an amplitude of the noise-induced signals and an amplitude of the cardiac electrical signals in response to sensing at least one of the noise signals independently of the electrical signals sensed using the sensing vector that includes the at least one electrode on the implantable medical lead and determining that the magnetic field exceeds the threshold strength.

22. The non-transitory computer-readable medium of claim 21, wherein the instructions to adjust the sensing threshold comprise instructions that cause the implantable medical device to adjust the sensing threshold in response to sensing a first one of the noise signals independently of the electrical signals sensed using the sensing vector that includes the at least one electrode on the implantable medical lead.

23. The non-transitory computer-readable medium of claim 21, further comprising instructions that, when executed, cause an implantable medical device to:
compare an amplitude of the noise-induced electrical signals sensed using the sensing vector that includes the at least one electrode on the implantable medical lead to a threshold noise amplitude;
transition to a noise operating mode when the amplitude of at least one of the noise-induced electrical signals exceeds the threshold noise amplitude; and
adjust the sensing threshold of the sensing module when the amplitude of at least one of the noise-induced electrical signals does not exceed the threshold noise amplitude.

24. The non-transitory computer-readable medium of claim 21, further comprising instructions that, when executed, cause an implantable medical device to:
determine that no noise signals have been detected independently of the electrical signals sensed using the sensing vector that includes the at least one electrode on the implantable medical lead for a predetermined period of time; and
reset the sensing threshold to a value corresponding to the value used prior to detecting the noise signals.

* * * * *